United States Patent [19]

Schulz et al.

[11] 4,153,785
[45] May 8, 1979

[54] POLYAMIDE RESINS FROM DILACTONES

[75] Inventors: Johann G. D. Schulz, Pittsburgh; Anatoli Onopchenko, Monroeville; Edward T. Sabourin, Allison Park, all of Pa.

[73] Assignee: Gulf Research & Development Company, Pittsburgh, Pa.

[21] Appl. No.: 897,682

[22] Filed: Apr. 19, 1978

Related U.S. Application Data

[63] Continuation-in-part of Ser. No. 748,686, Dec. 8, 1976, Pat. No. 4,104,281.

[51] Int. Cl.² .............................................. C08G 69/26
[52] U.S. Cl. .................................. 528/347; 528/335; 528/339; 528/341; 528/336; 528/354
[58] Field of Search ................ 528/347, 335, 339, 341

[56] References Cited

U.S. PATENT DOCUMENTS

| | | | |
|---|---|---|---|
| 2,079,325 | 5/1937 | Larchar et al. | 260/343.3 |
| 3,332,964 | 7/1967 | McCraken et al. | 260/346.3 |
| 3,895,037 | 7/1975 | Onopchenko et al. | 260/346.3 |

Primary Examiner—Harold D. Anderson

[57] ABSTRACT

This invention relates to novel isometric polyamide resins.

12 Claims, No Drawings

POLYAMIDE RESINS FROM DILACTONES

This application is a continuation-in-part application of our Application Serial No. 748,686 filed Dec. 8, 1976, entitled Process for Preparing Novel Isomeric Dicarboxy, Di(hydroxymethyl) Diphenylmethane Dilactones, now U.S. Pat. No. 4,104,281, dated Aug. 1, 1978.

FIELD OF THE INVENTION

This invention relates to novel isomeric polyamide resins, namely, poly-N-omega-aminoalkyl [methylene-bis-(2-hydroxymethylbenzamides)].

DESCRIPTION OF PRIOR ART

We are not aware of pertinent prior art.

SUMMARY OF THE INVENTION

The specific novel isomeric polyamide resins claimed herein can be defined as follows:

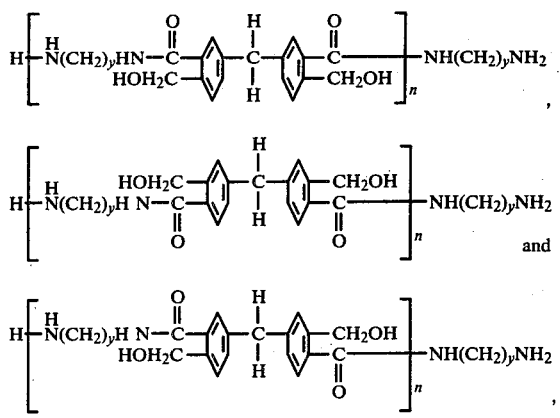

wherein y is an integer ranging from about 2 to about 12, preferably about 2 to about 6, most preferably 2, and n is an integer ranging from about 20 to about 100, or even greater, preferably about 30 to about 80.

The novel isomeric polyamide resins defined above can be prepared by reaction of any one or combination of lactones defined and claimed in our said copending application Ser. No. 748,686, namely, 3,3'-dicarboxy,4,4'-di(hydroxymethyl),diphenylmethane dilactone, 4,4'-dicarboxy,3,3'-di(hydroxymethyl),diphenylmethane dilactone or 4,3'-dicarboxy,3,4'-di(hydroxymethyl),diphenylmethane dilactone, or mixtures thereof, with alpha,omega-diaminoalkanes, or mixtures of alpha,omega-diaminoalkanes, of the following formula:

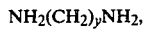

wherein y is an integer as defined above. Specific examples of alpha,omega diamino-alkanes that can be used include 1,2-diaminoethane, 1,3-diaminopropane, 1,4-diaminobutane, 1,6-diaminohexane, 1,12-diaminododecane, etc. For each mol of the dilactone there can be used from about 0.4 to about 10 mols, preferably about 0.4 to about one mol, but most preferably about 0.4 to about 0.6 mols of the alpha,omega-diaminoalkane.

The reaction is carried out in an inert atmosphere, for example, in a nitrogen-, helium- or argon-containing atmosphere. When relatively small amounts of the alpha, omega diaminoalkane are used, it is preferred to have a solvent present. Because of the relatively low solubility of the dilactones in most solvents, a powerful solvent, such as N-methylpyrrolidine, dimethylacetamide, dimethyl sulfoxide or dimethyl formamide, is preferred. It may also be desirable to incorporate into the reaction mixture unreactive hydrocarbon solvents, such as benzene, toluene, xylenes and the like to assist in moderating the temperature of reaction and as an azeotroping agent to facilitate removal of water of reaction from the reaction zone. The temperature of the reaction can be in the range of about 75° to about 200° C., preferably about 100° to about 150° C. While operation at atmospheric (ambient) pressure is preferred, the pressure can be from about atmospheric to as high as about 500 pounds per square inch gauge (34 kilograms per square centimeter), or even higher. Reaction time can be in the range of about 10 minutes to about 200 hours, preferably about one to about 24 hours.

Completeness of the reaction can be followed by the disappearance of the dilactone by any suitable means, such as gas chromatography or infrared spectroscopy. Isolation of the resin polyamide can be accomplished by distillation of the solvents under reduced pressure. The distillation residue is ground to a powder, washed with a solvent, such as isopropanol, to obtain the novel resin polyamide claimed herein.

DESCRIPTION OF PREFERRED EMBODIMENTS

EXAMPLE I

Following the procedure of Run No. 2 in our Application Ser. No. 748,686 an isomeric mixture of dicarboxy,di(hydroxymethyl)diphenylmethane lactones was prepared as follows. A nickel catalyst (NI 0104P, manufactured by Harshaw Chemical Company, Cleveland, Ohio) was pretreated in a one-liter autoclave by heating the same in tetrahydrofuran at a temperature of 190° C. and under a hydrogen pressure of 1000 pounds per square inch gauge (68 kilograms per square centimeter) for a period of 30 minutes. The reaction mixture was then cooled to room temperature (26° C.) and depressured to atmospheric pressure and benzophenone-3,4,3',4'-tetracarboxylic dianhydride (BTDA) was added thereto. The resulting reaction mixture, containing 150 grams BTDA, 15 grams of pretreated nickel catalyst and 500 milliliters of tetrahydrofuran, was heated at a temperature of 200° C. and under a hydrogen pressure of 1050 pounds per square inch gauge (71 kilograms per square centimeter) for a period of 30 minutes. At the end of the reaction period the reaction mixture was cooled to room pressure, depressured to atmospheric pressure and the contents thereof were filtered to separate catalyst and unreacted BTDA therefrom. The filtrate was then concentrated from about one-third to about one-quarter of its volume by heating in a rotary evaporator. The resultant filtrate was filtered to recover crystalline product and the latter was twice crystallized from ethyl acetate to recover a purer lactone product. NMR and IR studies of the recovered crystalline product disclosed the presence of the following three isomeric dilactones: (1) 3,3'-dicarboxy,4,4'-di(hydroxymethyl),diphenylmethane dilactone, (2) 4,4'-dicarboxy,3,3'-di(hydroxymethyl), diphenylmethane dilactone and (3) 4,3'-dicarboxy,3,4'-di(hydroxymethyl),diphenylmethane dilactone. Analysis showed 50 percent conversion of BTDA and a yield of the isomeric mixture of the dilactones of 42 percent. The melting point of the mixture of the dilactones was 182°–184°

C., its neutral equivalent 145, its carbon content 72.42 percent and its hydrogen content 4.50 percent.

EXAMPLE II

A total of 28 grams of a mixture of dilactones prepared in Example I and six grams of ethylene diamine were charged into a flask containing 100 milliliters of N-methylpyrollidine and five grams of benzene. The flask was fitted with a Dean-Stark trap filled with 50 milliliters of benzene. The reaction mixture was heated under reflux (around 140° C.) for 4.5 days. A total of 4.3 grams of water was collected. After stripping off N-methylpyrollidine under reduced pressure, the residue amounted to 30.2 grams. The crude polymer was ground into powder, washed several times with about 100-milliliter portions of boiling isopropanol to remove last traces of solvent and air dried for six hours, followed by drying in a vacuum at 100° C. for 10 hours. Analysis of the product indicated the reaction proceeded as follows:

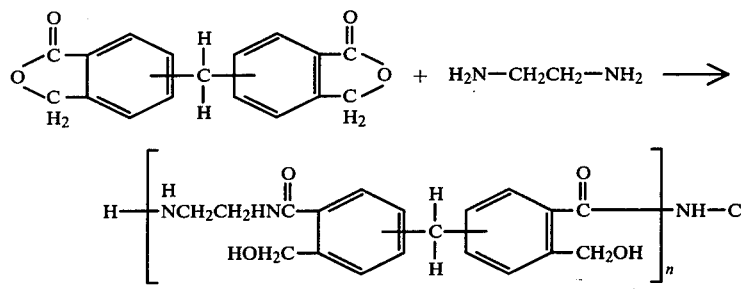

The resin was found to have a molecular weight slightly in excess of 10,000 and distinguished itself by its virtual insolubility in conventional solvents, such as methanol, acetone, ethyl acetate, tetrahydrofuran and benzene. The molten resin was drawn into flexible fibers capable of being cold drawn to impart additional mechanical strength thereto suitable for the preparation of fabrics therefrom.

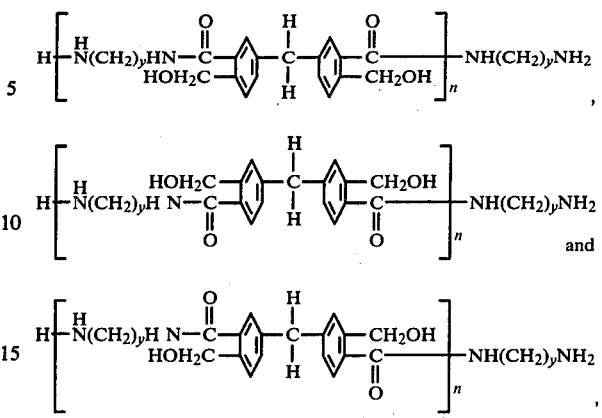

wherein y is an integer ranging from about 2 to about 12, and n is an integer ranging from about 20 to about 100.

2. The polyamide of claim 1 wherein y is an integer ranging from about 2 to about 6 and n is an integer ranging from about 30 to about 80.

3. The polyamide of claim 1 wherein y is the integer 2 and n is an integer ranging from about 30 to about 80.

4. The polyamide of claim 1 defined by the following formula:

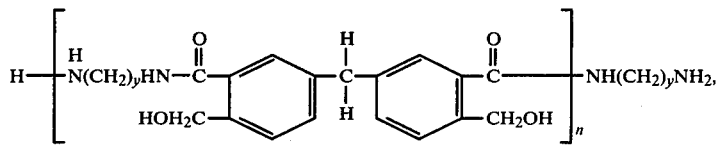

Obviously, many modifications and variations of the invention as hereinabove set forth can be made without departing from the spirit and scope thereof, and therefore only such limitations should be imposed as are indicated in the appended claims.

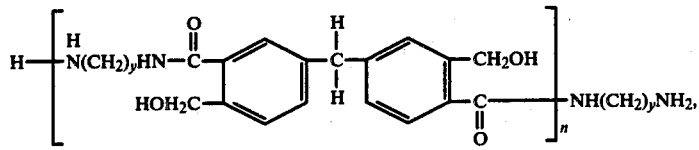

We claim:

1. A poly-N-omega-aminoalkyl[methylene-bis-(2-hydroxymethylbenzamide)] resin selected from the group consisting of wherein y is an integer ranging from about 2 to about 12 and n is an integer ranging from about 20 to about 100.

5. The polyamide of claim 4 wherein y is an integer ranging from about 2 to about 6 and n is an integer ranging from about 30 to about 80.

6. The polyamide of claim 4 wherein y is the integer 2 and n is an integer ranging from about 30 to about 80.

7. The polyamide of claim 1 defined by the following formula:

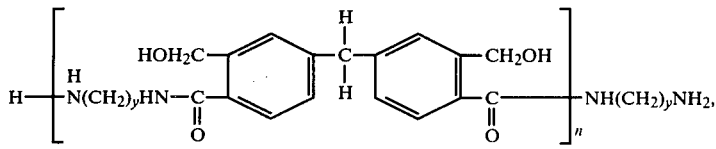

wherein y is an integer ranging from about 2 to about 12 and n is an integer ranging from about 20 to about 100.

8. The polyamide of claim 7 wherein y is an integer ranging from about 2 to about 6 and n is integer ranging from about 30 to about 80.

9. The polyamide of claim 7 wherein y is the integer 2 and n is an integer ranging from about 30 to about 80.

10. The polyamide of claim 1 defined by the following formula:

wherein y is an integer ranging from about 2 to about 12 and n is an integer ranging from about 20 to about 100.

11. The polyamide of claim 10 wherein y is an integer ranging from about 2 to about 6 and n is an integer ranging from about 30 to about 80.

12. The polyamide of claim 10 wherein y is the integer 2 and n is an integer ranging from about 30 to about 80.

* * * * *